United States Patent [19]

Manz

[11] Patent Number: 5,180,480
[45] Date of Patent: Jan. 19, 1993

[54] APPARATUS FOR THE PREPARATION OF SAMPLES, ESPECIALLY FOR ANALYTICAL PURPOSES

[75] Inventor: Andreas Manz, Basel, Switzerland

[73] Assignee: Ciba-Geigy Corporation, Ardsley, N.Y.

[21] Appl. No.: 819,708

[22] Filed: Jan. 13, 1992

[30] Foreign Application Priority Data

Jan. 28, 1991 [EP] European Pat. Off. ............ 91810062

[51] Int. Cl.$^5$ ...................... G01N 27/26; B01D 57/02
[52] U.S. Cl. ................................. 204/299 R; 204/180.1
[58] Field of Search .................... 204/302, 299 R, 301, 204/183.2; 210/748

[56] References Cited

U.S. PATENT DOCUMENTS 3,364,481  8/1969  Richman ........................ 204/299 R
3,847,773  11/1974 Snyder .......................... 204/299 R
4,061,560  12/1977 Hannig .......................... 204/299 R

FOREIGN PATENT DOCUMENTS 0171676  2/1986  European Pat. Off. .
0256552  2/1988  European Pat. Off. .

OTHER PUBLICATIONS

Howery et al., Journal of Chromatographic Science, vol. 10, Sep., 1972, pp. 557-559.
McCreight et al., AIAA Journal, vol. 16, No. 5, May, 1978.

Primary Examiner—John Niebling
Assistant Examiner—John S. Starsiak, Jr.
Attorney, Agent, or Firm—Marla J. Mathias; JoAnn Villamizar; John T. Miller

[57] ABSTRACT

An apparatus (1) is used for the preparation or extraction of samples, especially for analytical purposes, from a liquid or using a carrier liquid, where only very little liquid and substrate is available or is to be used and where the sample separation is to be carried out very quickly. For this, the apparatus (1) comprises, etched or machined into a plate-shaped body (8), an essentially planar flow bed (10) which has inlets and outlets arranged at opposing ends in the direction of flow, and is covered and sealed on the processing side of the plate-shaped body (8) by a further plate, so that the flow bed (10), which has an approximately groove-shaped flat cross-section, is sealed on all sides. There extend parallel to the flow bed (10), but also machined or etched into the plate-shaped body (8), electrode chambers (13), which are connected by way of electrodes (13b) to a current source (13a) in order to generate an electric field in the flow bed (10) transversely to the direction of flow. The electrode chambers (13) are connected to the flow bed (10) by way of very fine channels (14) extending transversely to the direction of flow which permit voltage transmission but practically no transport of material, that is to say act in a similar manner to membranes. Etching technology permits a miniaturized construction of the apparatus (1).

16 Claims, 8 Drawing Sheets

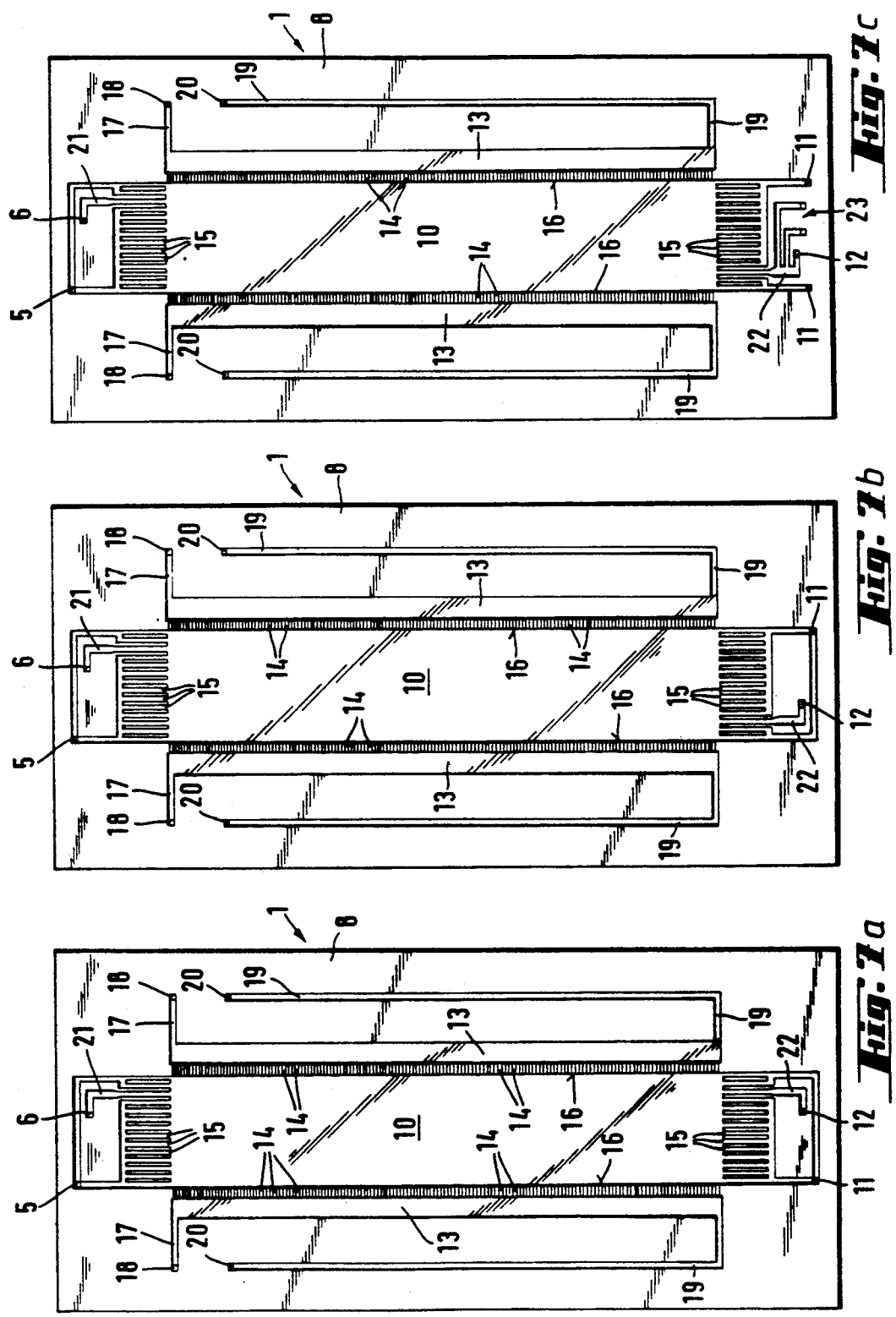

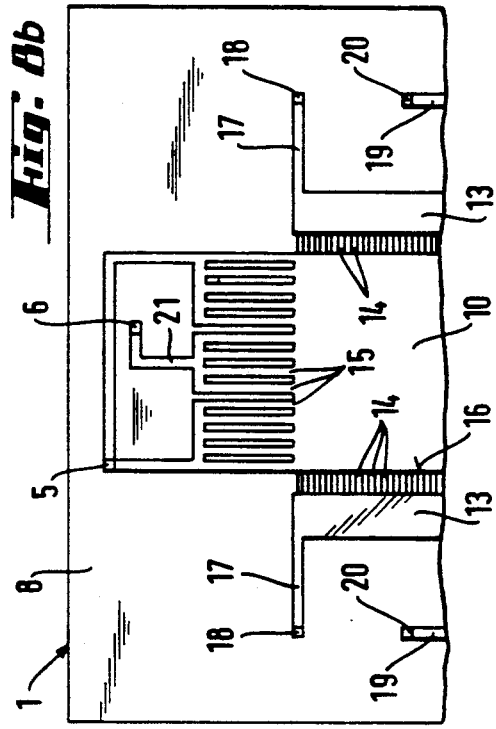
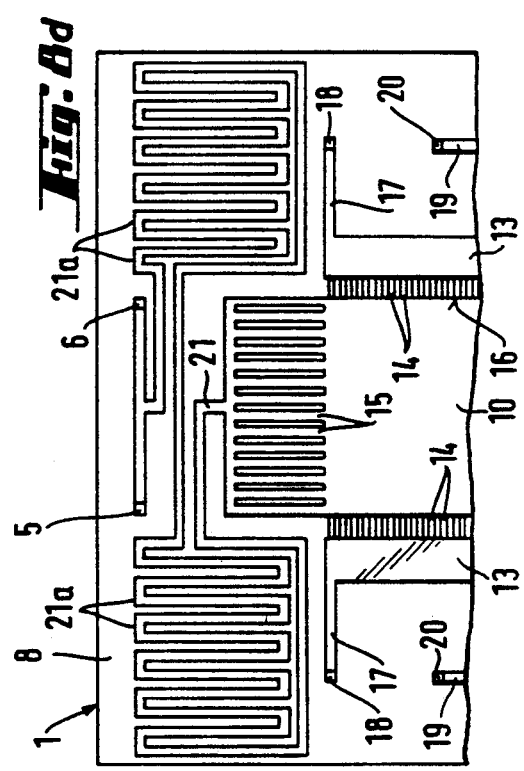
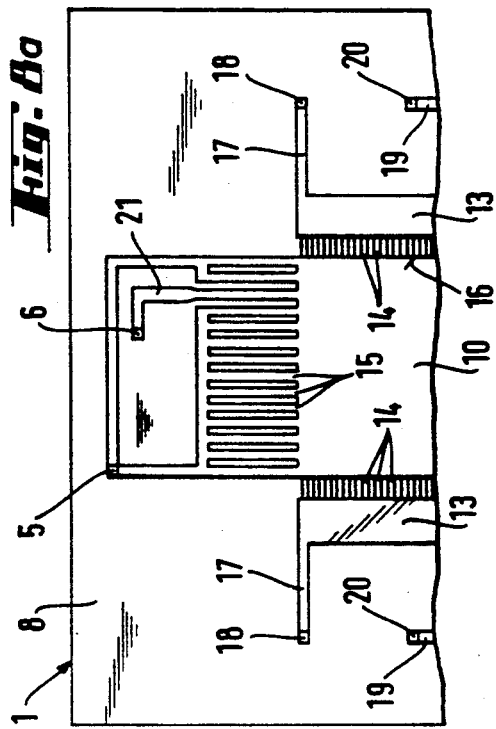
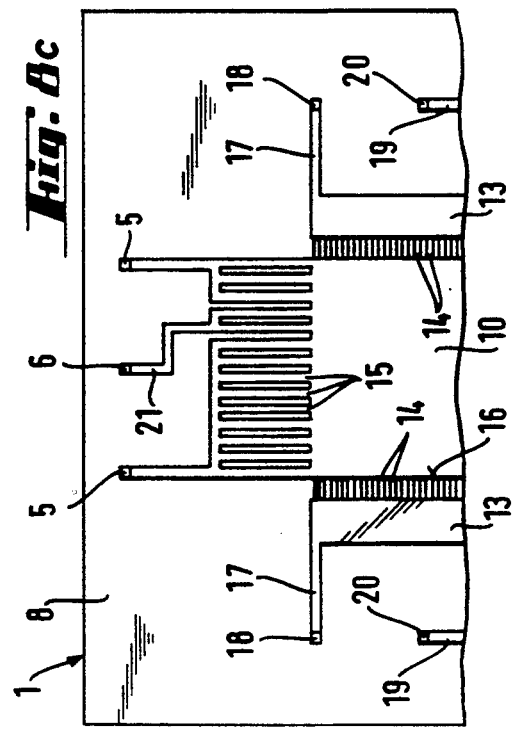

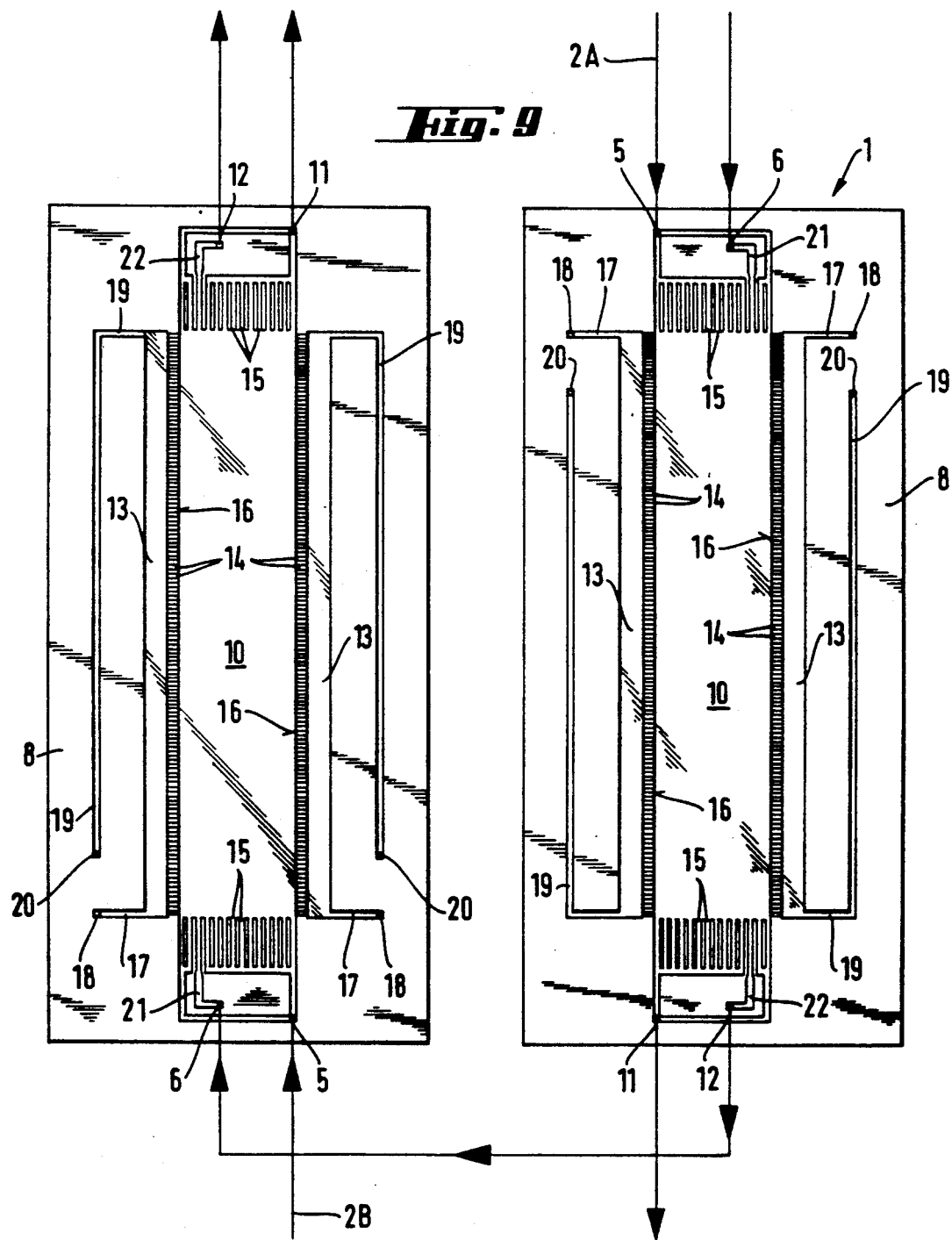

APPARATUS FOR THE PREPARATION OF SAMPLES, ESPECIALLY FOR ANALYTICAL PURPOSES

BACKGROUND OF THE INVENTION

1. Field of the Invention

The invention relates to an apparatus for the preparation or extraction of samples, especially for analytical purposes, from a liquid or using a carrier liquid.

2. Description of the Related Art

The separation of a sample in this manner is known, for example, in flow-injection analysis in which filtration, dilution, concentration, extraction, chemical reaction or some other known procedure is carried out. There are difficulties, however, in such a preparation or extraction or separation of samples from liquid, aqueous or biological-aqueous media, since the separation of sample molecules according to electrical charge or according to ionic mobilities is generally difficult or even impossible.

OBJECTIVES OF THE INVENTION

The problem therefore arises of providing an apparatus of the type mentioned at the beginning that enables as far as possible the continuous separation of samples in order to extract exclusively molecules of a particular charge or electrophoretic mobility or ionic mobility, for which the throughput time is very short and with which small amounts of starting material are sufficient to obtain an adequately large sample.

SUMMARY OF THE INVENTION

The solution to this problem is as follows: the apparatus comprises, etched or machined into an approximately plate-shaped body, an essentially planar flow bed having at least one inlet and one outlet, which are arranged at opposing ends in the direction of flow, and having a cover covering the margins of the flow bed and the bed itself; recesses that serve as electrode chambers and are connected to current sources are etched or machined into the plate-shaped body at both sides of and parallel to the flow bed; and there are provided between the flow bed and the electrode chambers fine channels which are arranged adjacent to one another and extend transversely to the direction of flow and to the direction in which the flow bed extends.

Surprisingly, therefore, the apparatus uses for the sample extraction the process known from free-flow electrophoresis. That process has hitherto not been suitable for extracting samples for use for analytical purposes, since it has been used to extract proteins or similar substances, and the apparatuses provided for that purpose are too large and too expensive for sample separation. The amounts of material required for the hitherto known apparatuses are so large that they frequently exceed those amounts from which a sample has to be extracted and, in any case, in view of the starting amounts of substrate required, the cost of the sample extraction would be too high and also the time taken would be too long. By means of a flow bed machined or etched into a plate-shaped body, however, the arrangement can be miniaturised in such a manner that desired samples can be obtained in a very short time and using a very small amount of material. Advantageously, a very uniform, planar and shallow flow bed can be produced in which flow ratios extremely favourable for electrophoresis can be created.

The cover covering the margins of the flow bed and the electrode chambers may be an especially smooth plate which—for example by the action of heat, by bonding, by sticking or by fusing or the like—can be joined to the body comprising the flow bed. Consequently, the manufacture of the apparatus is altogether relatively simple and low in cost.

The miniaturisation of the apparatus already mentioned may, for example, entail the planar flow bed having a length in the direction of flow of the substrate of approximately 1 mm to approximately 50 mm or approximately 60 mm or approximately 70 mm or optionally approximately 100 mm or also dimensions inbetween, and having a width between approximately 0.1 mm and approximately ½ cm or approximately 1 cm or inbetween and, finally, having a depth—that is to say the inside dimension between the base of the flow bed and the cover plate—of from approximately 1 micrometer to approximately 50 micrometers. The values for each dimension do not have to be exactly proportional to the limits specified above, that is to say, for example, a 25 mm flow bed may also be only 0.1 mm or perhaps 3 mm or 4 mm wide. A large number of possible variations therefore exists within the dimensions specified so that an apparatus of a size that is advantageous for a particular purpose can be created.

The inlet and the outlet may each be channels approximately 1 micrometer to approximately 100 micrometers wide and/or deep. The dimensions of the inlet and outlet can consequently be adapted to the miniaturised dimensions of the flow bed itself, so as to produce the desired flow ratios.

The cross-section of the channels that extend transversely to the flow bed and join the flow bed to the electrode chambers may be smaller than that of the inlet and outlet channels and, especially, may be so small that, apart from the voltage transmission, there is virtually no transport of material through those channels. In the relatively large apparatuses for electrophoresis it is known to shield the electrode chambers from the flow bed by membranes that prevent transport of material to the electrode chambers. It would not, however, be possible to arrange membranes in the miniaturised apparatus according to the invention, because the fixing and sealing of such membranes would lead to insuperable difficulties. A special measure was therefore required in order, without the use of membranes, nevertheless to exclude the transport of material to the electrode chambers as far as possible, but to allow voltage transmission within the liquid.

To this end, the transverse channels may be arranged in parallel and directly adjacent to one another along the flow bed and their length may especially correspond approximately to the width of the electrode chambers or be shorter than that width. As a result of the arrangement of these very small channels one directly adjacent to another, the desired connection for the voltage transmission to the electrode chambers is in practice provided over a large length or over the entire length of the flow bed, whilst at the same time the transport of material is virtually excluded.

It is advantageous for the channel-like electrode chambers—which extend essentially parallel to the flow bed—to have supply or discharge channels to enable continuous washing. These channels are especially machined or etched into the body comprising the flow bed and are covered by the cover. Consequently, all important recesses, such as the flow bed itself, the electrode chambers and the various channels, are etched or machined into the same plate-shaped body, so that they are also jointly sealed by the cover plate, thus making it possible to provide a compact and miniaturised apparatus in which, in a very small space and with very small amounts of substrate, samples can be extracted on the basis of their electric charge and ionic mobility.

The inlet and outlet channels which, especially, are also etched or machined into the body, may be connected to an inlet for carrier liquid and oriented upstream and downstream of the flow bed, respectively, in the direction of flow. As a result, a sample inlet may be connected by way of a supply line to one or several inlet channels especially away from the longitudinal centre line of the flow bed.

Similarly, a sample outlet may be connected to outlet channels and may be arranged as a direct extension of the sample inlet line or lines—for electrically neutral ions or sample molecules—or, especially for zone electrophoresis, opposite the sample inlet on the other side of the longitudinal centre line of the flow bed.

Another variation, for carrying out field jump electrophoresis, comprises the arrangement of the sample inlet at the centre of the assembly of inlet channels to the flow bed.

Instead of that it is also possible, for isotachophoresis, to provide an eccentric line for supplying the sample to the inlet channels.

Finally, for electrophoresis with isoelectric focussing, in the region of the inlet channels, especially at both sides of the inlet of the supply line, the supply line may be wound or guided to and fro about its path, and such windings may be arranged at both sides of the inlet channels in order to produce the focussing field.

There is consequently a large number of possible ways of separating a wide variety of samples depending on the charge or ionic mobility that exists in the desired samples. It is also possible for an outlet channel for uncharged or neutral compounds to be arranged approximately in alignment with the inlet channel at the opposite end of the flow bed, and for an outlet for charged compounds or ions to be arranged laterally displaced with respect to the longitudinal centre line of the flow bed and with respect to the inlet.

The apparatus according to the invention permits, for the extraction of complex samples or the processing of very complex mixtures which may consist of many different substances, an arrangement in which the outlet of a first flow bed is connected to the inlet of at least a second flow bed. Even connection of that second flow bed to a further flow bed and the corresponding processing and application of electrical fields is possible.

It should also be mentioned that the plate comprising the flow bed and/or its cover plate may consist of silicon and/or quartz and/or glass. These are materials that are well suited to etching, and therefore permit the desired miniaturised arrangement of the flow bed and the various channels, and that furthermore remain insensitive and resistant to attack by a wide variety of substances but are nevertheless relatively low in cost.

To summarise, an apparatus is provided with which neutral molecules or ions of a particular charge can be extracted as a sample from a complex sample mixture, it being possible for those molecules, which form a sample, for example for analytical purposes, to be collected continuously.

Consequently, it is possible, for example, to measure the components concerned continuously in an analysis system, for example when monitoring processes or in connection with the protection of the environment. It is advantageous that extremely small initial amounts of the substrate to be examined are sufficient and that there is no risk of the apparatus becoming blocked, as has been the case hitherto in continuous sample extraction using filters. The throughput time may be of the order of seconds. Also, only a very small amount of electrolyte is required. This is of correspondingly considerable advantage also as regards the disposal of residual substances.

BRIEF DESCRIPTION OF THE DRAWINGS

Several embodiments of the invention are described in detail below with reference to the drawings.

The drawings, some of which are diagrammatic, are as follows:

FIGS. 7a-c show three different possible arrangements of outlets for uncharged compounds or ions, one of the arrangements having a conductive detector, for example a pair of electrodes, in the region of an outlet, FIGS. 8a-d show four different possible arrangements of the sample inlets and supply lines to the assembly of inlet channels, FIG. 9 shows an embodiment in which two plate-shaped bodies having a flow bed are arranged in series one after the other, but each flow bed has its own inlet for carrier liquid.

DETAILED DESCRIPTION OF THE INVENTION

Figure 1:
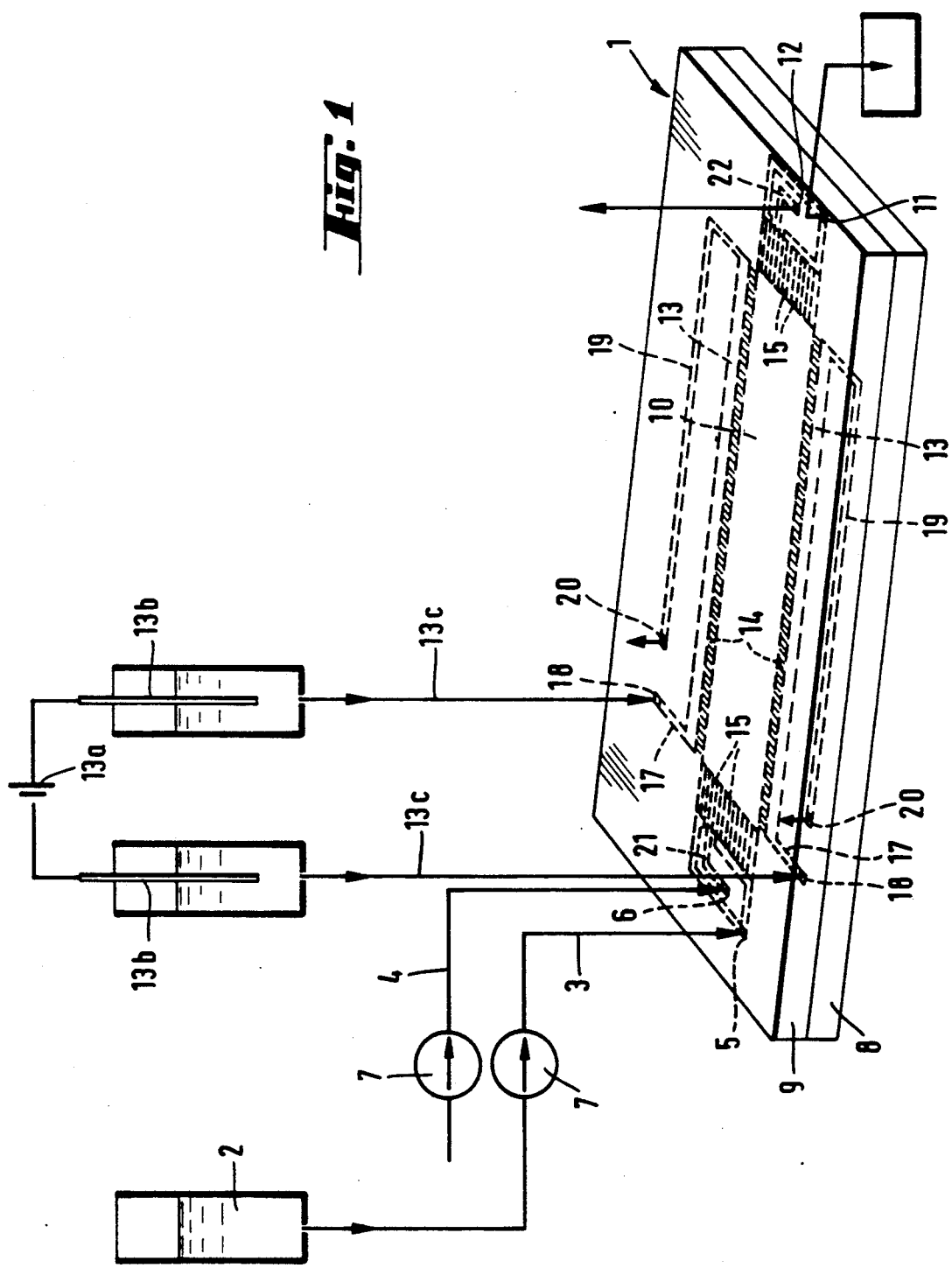
FIG. 1 shows an apparatus for the preparation or extraction of samples from liquids, having a plate-shaped body, in the interior of which a flow bed, electrode chambers and channels are arranged, having electrodes and electrolytic solution lines, which are connected by a voltage source, leading to that body, and also having pumps for supplying a whole sample and a carrier liquid.
Figure 2:
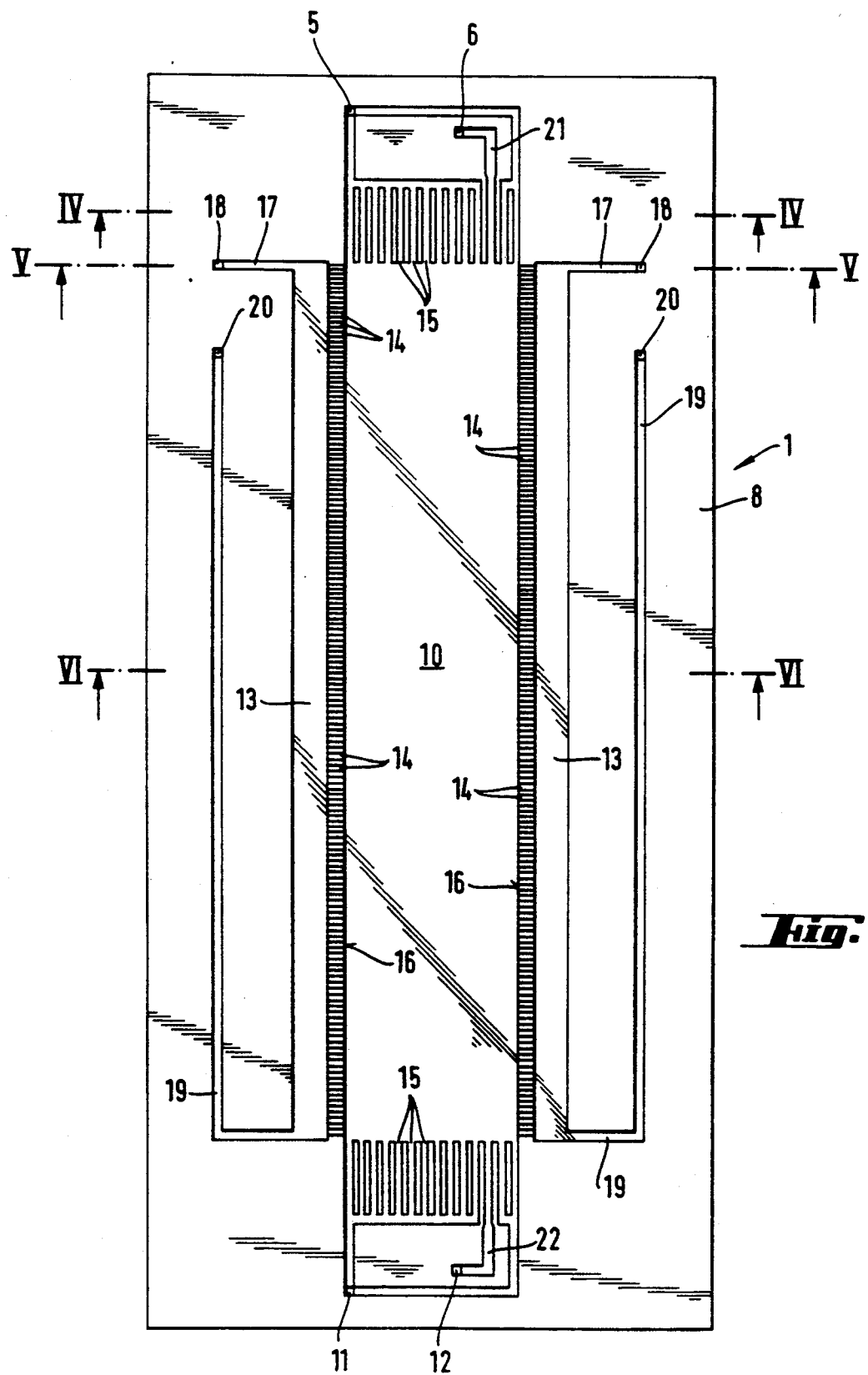
FIG. 2 is a plan view of the actual apparatus and of its plate-shaped body with the flow bed, the channels and electrode chambers.

An apparatus 1, designated as a whole by 1, and shown clearly especially in FIG. 2 and in FIGS. 3 to 6, is used to prepare and extract samples, for example for analytical purposes, from a liquid or a liquid mixture using a carrier liquid 2. It can be seen both in FIG. 1 and in FIG. 2 that the carrier liquid 2 and the whole sample itself have different supply lines 3 and 4 to different inlets 5 and 6. Pumps 7 may be arranged along the lines 3 and 4 in order to convey the liquids.

The apparatus 1 itself has an essentially plate-shaped body 8 covered by a smooth plate 9 as a cover for recesses which are etched or machined into the plate 8 and can be seen clearly especially in FIGS. 2 to 6.

The plate-shaped body 8, and thus the apparatus 1, has especially a machined or etched planar bed, that is to say a flow bed 10, as the actual separating chamber. At opposite ends in the direction of flow according to the broad arrows PF 1 in FIGS. 3 and 10, this bed has inlets 5 and 6 for carrier liquid 2 and sample substrate, and outlets 11 and 12, the outlet 11 being for the carrier liquid as well as remains of the sample, and the outlet 12 serving to remove the separated sample. According to FIGS. 3 to 6, the cover plate 9 covers the entire plate-shaped body 8 and thus the margins of the flow bed 10 and all the associated recesses machined in the body 8 which are still to be described in detail. It may be seen from FIGS. 3, 5 and 6 that, parallel to and on both sides of the flow bed 10, recesses are etched or machined into the plate-shaped body 8 which act as electrode chambers 13 and are connected to a current source 13a (FIG. 1) by way of corresponding electrodes 13b and an electrolyte solution and its supply lines 13c. As shown in FIGS. 2 and 6, fine parallel channels 14 extending transversely to the direction of flow and to the direction in which the flow bed 10 extends, are arranged in a row adjacent to one another, between the flow bed 10 and the electrode chambers 13 running parallel thereto, and, as shown in FIG. 2, are arranged along the entire length of the flow bed 10.

The plate 9 covering the margins of the flow bed 10 and the bed itself, as well as the electrode chambers 13 and the channels 14, may be joined, for example by bonding, to the plate-shaped body 8 comprising the flow bed 10 and the other recesses.

Figure 3:
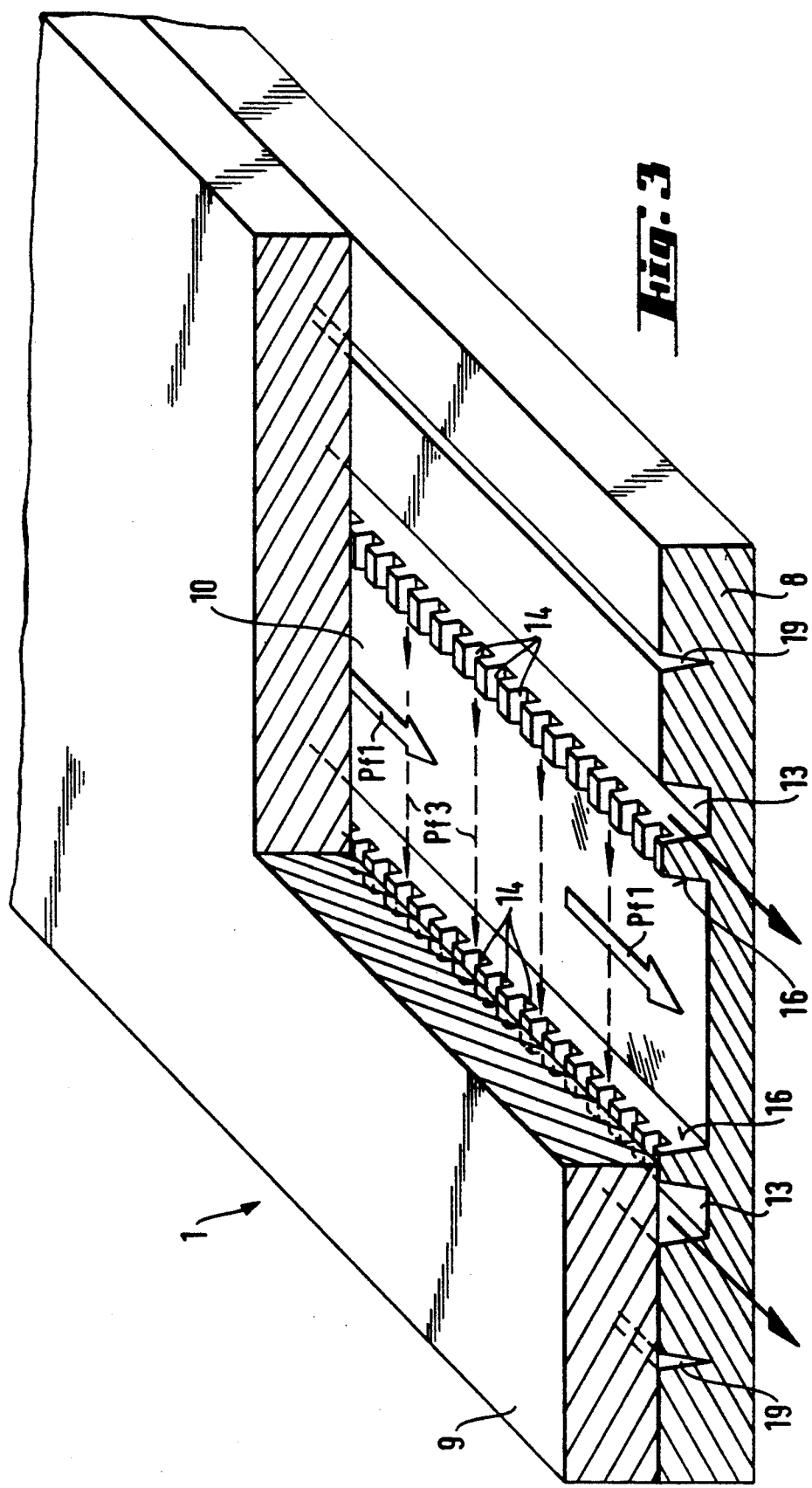
FIG. 3 is a diagrammatic representation, on a substantially enlarged scale, of a portion of an apparatus according to the invention, with the flow bed, the electrode chambers, washing channels and an upper cover plate.
Figure 4:
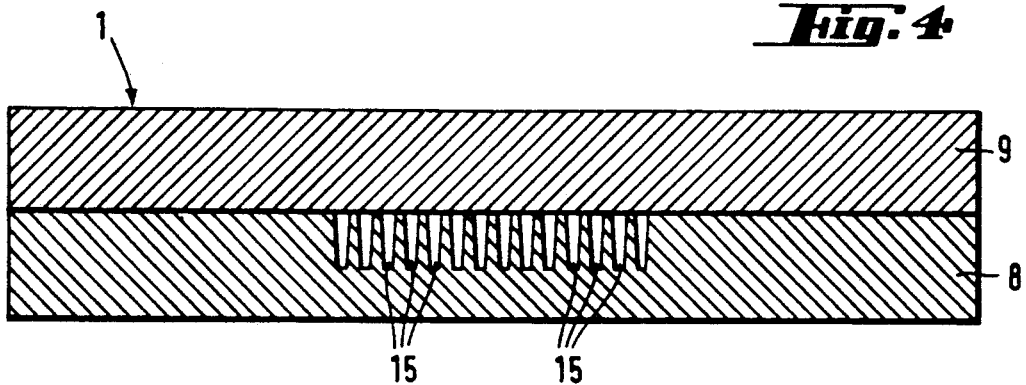
FIG. 4 is a cross-section, along the line IV—IV in FIG. 2, of the apparatus according to FIG. 2 in the region of the inlet channels into the flow bed.
Figure 5:
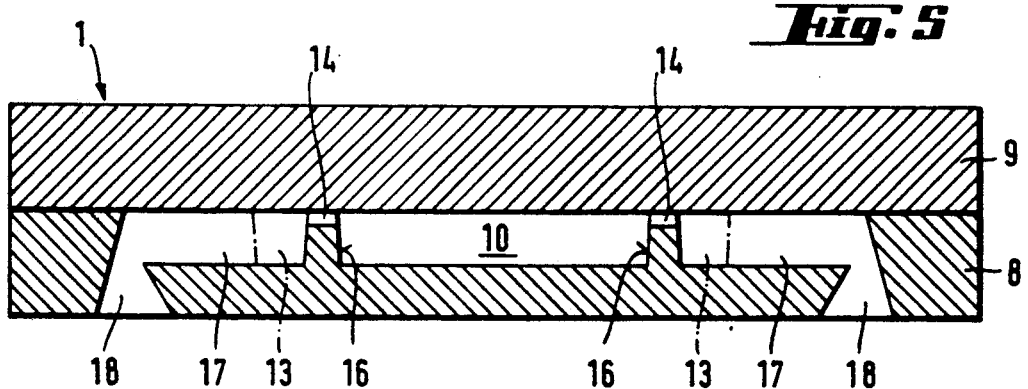
FIG. 5 is a cross-section corresponding to FIG. 4, along the line V—V in FIG. 2, through the beginning of the flow bed and through inlet channels serving to wash the electrode chambers.
Figure 6:
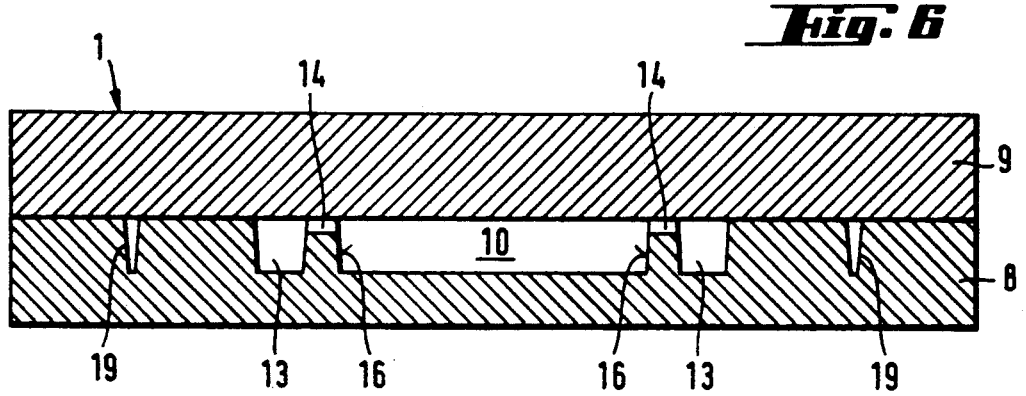
FIG. 6 is a cross-section along the line VI—VI in FIG. 2 through the flow bed and the electrode chambers and washing channels extending parallel thereto.

FIGS. 2 to 6 show clearly that altogether a very compact, planar, in the embodiment rectangular, apparatus 1 is produced which renders possible, with very small dimensions, an effective continuous separation of samples. For example, the flow bed 10—which according to FIGS. 3, 5 and 6 is of practically constant depth over its width—may have a length of approximately 1 mm to approximately 50 mm or also approximately 60 mm or 70 mm, even, depending on the particular application, 80 mm or optionally approximately 100 mm, and its width, which can be seen clearly in FIGS. 5 and 6, may lie between approximately 0.1 mm and approximately half a centimeter or also approximately a whole centimeter or inbetween, whilst the depth of the flow bed 10, already mentioned, may be from approximately 1 micrometer to approximately 50 micrometers. Consequently the overall dimensions of the apparatus are very small and, especially, the volume of the flow bed 10 is so small that only very small amounts of substrate and carrier liquid are required for the production of a sample for analytical purposes. There are provided as the actual inlet and outlet to the flow bed 10 respective assemblies of fine, parallel channels 15, which are approximately 1 micrometer to approximately 100 micrometers wide and/or deep and the shape and size of which relative to the other recesses can be seen in the cross-section in FIG. 4.

The dimensions of the channels 14, which extend transversely to the flow bed 10 and connect the flow bed 10 to the electrode chambers 13, are smaller than those of the inlet and outlet channels 15, which can be seen in a cut-away portion of the apparatus 1 shown in FIG. 3, and in FIGS. 5 and 6. These transversely extending channels 14 are so small that, apart from the voltage transmission, there is virtually no transport of material through these channels 14, that is to say, the voltage necessary for the current flow in the electrolyte solution can be transmitted through these fine or very fine channels but virtually no transport of material is possible.

These fine channels 14 arranged along the flow bed 10 are each of a length that corresponds approximately to the width of the electrode chambers 13 or—as can be seen in FIGS. 3 and 6—is even shorter than that width. It is also clear in FIGS. 5 and 6 that these fine transversely extending channels 14 are arranged at the top of the flow bed, whilst the flow bed is for the most part bounded by its side walls 16. By this means, too, the transport of material from the flow bed 10 into the electrode chambers 13 is prevented. At the same time, the possibility thus presents itself of machining the flow bed 10, the channels 14 and the electrode chambers 13 into the plate-shaped body 8 all from the side that will later be covered and sealed by the plate 9. Both the plate-shaped body 8 and the plate 9 then have, on their facing surfaces, a constant planar shape which, in the case of the plate 8, is interrupted only by the flow bed 10 and the other recesses.

The channel-shaped electrode chambers 13 have supply channels 17—with inlet openings 18—visible in FIGS. 2 and 5, and furthermore discharge channels 19 for constant washing. These supply channels 17 and discharge channels 19, which in turn have outlets 20 corresponding to the inlet openings 18, are also etched or machined into the planar plate-shaped body 8 comprising the flow bed 10 and are covered by the cover plate 9.

According to FIG. 2, the inlet channels 15, which are likewise machined or etched into the plate-shaped body, are connected to the inlet 5 for carrier liquid 2 and are oriented upstream of the flow bed 10 in the direction of flow. Similarly, the outlet channels 15 are arranged downstream of the flow bed 10 in the direction of flow, as is visible especially in FIG. 2.

In addition, it can be seen especially clearly in FIG. 2, but also in FIGS. 7 and 8 as well, that the sample inlet 6 is connected by way of a supply line 21 to one or several inlet channels 15, which discharge into the flow bed 10 away from the longitudinal centre line thereof, preferably as shown in FIG. 2 or FIGS. 7 and 8a and 8c.

Analogously, a sample outlet line 22 is connected to outlet channels 15 and can occupy different positions relative to the supply line 21, as can be seen from FIGS. 7a, 7b and 7c as well as FIG. 9.

FIG. 2, FIG. 7a and FIG. 9 show arrangements in which the sample outlet line 22 is arranged as a direct extension of the sample inlet line or lines, so as to be able to receive and discharge uncharged or neutral compounds approximately in alignment with the inlet or supply line 21. For the discharge of charged compounds or ions, and especially the application of zone electrophoresis, the sample outlet line 22 according to FIG. 7b may, however, be arranged opposite to the sample inlet, laterally displaced with respect to that inlet and on the other side of the longitudinal centre line of the flow bed 10.

Whereas FIG. 8a again shows a sample inlet line 21 to an inlet channel 15 which is arranged to one side of the longitudinal centre line of the flow bed 10, FIG. 8b is an example of an arrangement in which the sample inlet line 21 is arranged in the centre of the assembly of inlet channels 15 to the flow bed 10, that is, virtually in alignment with the longitudinal centre line of the flow bed 10, so that this arrangement is suitable for carrying out field jump electrophoresis. The arrangement according to FIG. 8a is, as already mentioned, suitable for and intended for zone electrophoresis.

FIG. 8c shows an arrangement for isotachophoresis with an eccentric sample supply line 21 to the corresponding inlet channels 15 and two inlets 5 for different carrier liquids.

FIG. 8d shows, finally, that electrophoresis with isoelectric focussing in the region of the inlet channels 15 is also rendered possible with the apparatus according to the invention by, at both sides of the inlet of the supply line 21, winding that line repeatedly about its path, the windings 21a being arranged at both sides of the inlet channels 15 so as to enable the production of a focussing field. In this arrangement the carrier liquid and the sample are conveyed from their inlets 5 and 6 together, and then flow through the supply line 21 and the windings 21a.

In FIG. 7c, in addition a conductivity detector 23, in the form of a pair of electrodes, may be seen at the outlet channels.

Figure 10:
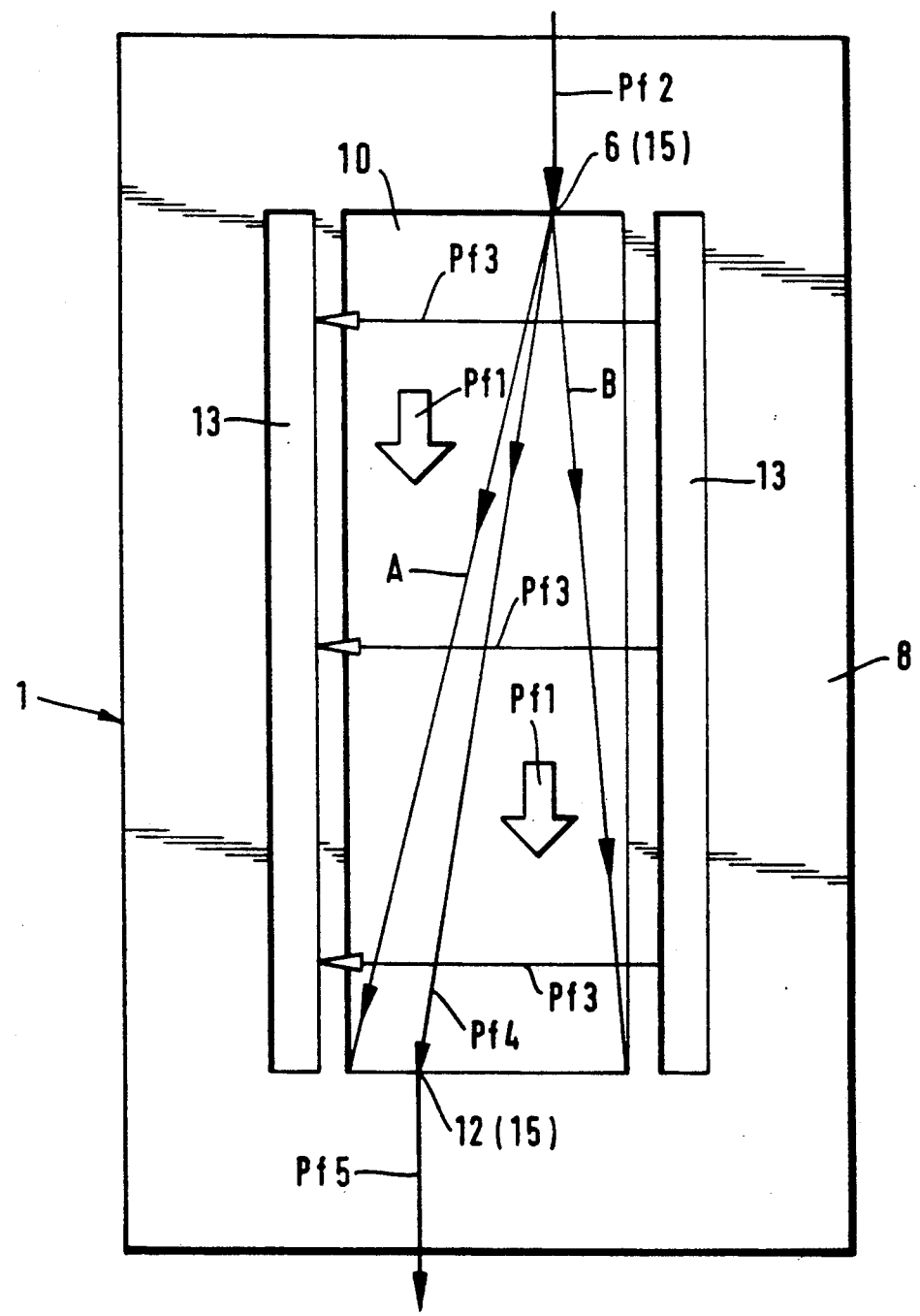
FIG. 10 is an outline drawing of the plate-shaped body comprising the flow bed, with arrows showing the direction of flow of the carrier liquid, the sample inlet, the deflection of the sample to its outlet and the direction of migration of various other components according to the electrical field indicated by further arrows.

The principle of operation of the apparatus 1 is represented diagrammatically in FIG. 10. The apparatus 1 can be seen in plan view. In the upper region the sample inlet 6 is indicated by the arrow Pf 2. Inside the apparatus 1, that is to say in the flow bed 10, the carrier liquid flows in the direction of the arrows Pf 1. An electric field is generated through the electrode chambers 13 in the direction of the arrows Pf 3. This results, in the course of the flow bed 10 and the flow, in the desired components from the sample drifting away in the direction shown by the inclined arrow Pf 4, so that the separated sample can be collected at the outlet according to arrow Pf 5. The other charged components are also deflected from the main flow in accordance with lines A and B and can be discharged through other outlet channels 15 that are not associated with the outlet for the separated sample. Depending on which component is to form the separated sample, the outlet channels collecting the sample must be arranged accordingly.

FIG. 9 shows an embodiment in which the sample outlet 12 of a first flow bed 10 is connected to the sample inlet 6 of at least a second flow bed 10, that is to say in practice two apparatuses 1 are arranged in series one after the other. As a result, complex mixtures of different substances can be processed.

For example, a carrier liquid 2A having a pH value of 7 and a sample mixture, for example of four components such as an amino acid, an anion, a cation and a neutral component, for example glucose, can be introduced at the inlet 5 of the first flow bed 10 or of the first apparatus 1.

At the sample outlet 12, the amino acid and the glucose can be collected and conveyed further, whilst at the outlet 11 for the carrier liquid the anion and the cation, for example bromide and iron, can be discharged as waste.

There are therefore introduced into the second fluidised bed only two components from the original sample mixture, that is the amino acid and the glucose components, a carrier liquid 2B that is different from the first carrier liquid 2A and that may have a pH value, for example of 9, also being introduced. The neutral component, for example the glucose, can then be discharged at the sample outlet 12.

To summarise, therefore, the apparatus 1 is one which allows a wide variety of uses in the extraction of samples and renders possible the desired extraction of a sample even from complicated or complex mixtures by arranging several such apparatuses in series. The entire apparatus 1 can be miniaturised, so that very small amounts of substrate are sufficient for carrying out the sample extraction. At the same time, the apparatus 1 is relatively low in cost, since the plate 8 comprising the flow bed 10, and the cover plate 9, may consist of silicon, quartz or glass and can be machined and joined by known processes.

The apparatus 1 is used for the preparation or extraction of samples, especially for analytical purposes, from a liquid or using a carrier liquid, where only very little liquid and substrate is available or is to be used, and where the sample separation is to be carried out very quickly. In addition, the apparatus 1 has, machined or etched into a plate-shaped body 8, an essentially planar flow bed 10 which has inlets and outlets at opposite ends in the direction of flow, and which is covered and sealed on the processing side of the plate-shaped body 8 by a further plate, so that the flow bed 10, which has an approximately groove-shaped flat cross-section, is sealed on all sides. There extend parallel to the flow bed 10, but also machined or etched into the plate-shaped body 8, electrode chambers 13, which are connected by way of electrodes 13b to a current source 13a in order to generate an electric field in the flow bed 10 transversely to the direction of flow. The electrode chambers 13 are connected to the flow bed 10 by way of very fine channels 14 extending transversely to the direction of flow which permit voltage transmission but practically no transport of material, that is to say act in a similar manner to membranes. Etching technology permits a miniaturised construction of the apparatus 1.

What is claimed is:

1. An apparatus (1) for the preparation or extraction of samples, for analytical purposes from a liquid and/or using a carrier liquid, wherein the apparatus (1) comprises, etched or machined into an approximately plate-shaped body (8), an essentially planar flow bed (10) having at least one inlet (5,6) and one outlet (11,12), which are arranged at opposing ends in the direction of flow, and having a cover covering the margins of the flow bed (10) and the bed itself, wherein recesses that serve as electrode chambers (13) and are connected to a current source (13a) are etched or machined into the plate-shaped body (8) at both sides of and parallel to the flow bed (10), and wherein there are provided between the flow bed (10) and the electrode chambers (13) fine channels (14) which are etched or machined into plate-shaped body (8), the fine channels (14) are arranged adjacent to one another and extend transversely to the direction of flow and to the direction in which the flow bed (10) extends.

2. An apparatus according to claim 1, wherein the cover covering the margins of the flow bed (10) and the electrode chambers (13) and the channels (14) connecting them is a smooth plate (9) which—by the action of heat, by bonding, by sticking or by fusing or the like—is joined to the body (8) comprising the flow bed (10).

3. An apparatus according to claim 1, wherein the planar flow bed (10) has a length in the direction of flow of the substrate of approximately 1 mm to approximately 50 mm or approximately 60 mm or optionally approximately 100 mm and a width between approximately 0.1 mm and approximately half a centimeter or approximately one centimeter or in between and the depth of the flow bed (10) is from approximately 1 micrometer to approximately 50 micrometers or 100 micrometers.

4. An apparatus according to claim to 3, wherein the inlet and the outlet may each comprise channels (15) from approximately 1 micrometer to approximately 100 micrometers wide and/or deep.

5. An apparatus according to claim 4, wherein the cross-section of the channels (14) that extend transversely to the flow bed (10) and join the flow bed (10) to the electrode chambers (13) is smaller than that of the inlet and outlet channels (15) and, is so small that, apart from the voltage transmission, there is virtually no transport of material through the channels (14).

6. An apparatus according to claim 1, wherein the transversely extending channels (14) are arranged in parallel and directly adjacent to one another along the flow bed (10) at right angles to the orientation of the flow bed (10) and of the electrode chambers (13), and their length corresponds approximately to the width of the electrode chambers (13) or is shorter than that width.

7. An apparatus according to claim 1, wherein the channel-shaped electrode chambers (13) have supply channels (17) or discharge channels (19) to enable continuous washing, which are machined or etched into the body (8) comprising the flow bed (10) and are covered by the cover (9).

8. An apparatus according to claim 1, wherein the inlet channels (15) which, are also etched or machined into the body, are connected to at least one inlet (5) for carrier liquid (2) and are each oriented upstream of the flow bed (10) in the direction of flow, and the outlet channels (15) are oriented downstream of the flow bed (10) in the direction of flow.

9. An apparatus according to claim 8, wherein a sample inlet (6) is connected by way of a supply line (21) to one or several inlet channels (15) away from the longitudinal centre line of the flow bed (10).

10. An apparatus according to claim 9, wherein a sample outlet line (22) is connected to outlet channels (15) and is arranged as a direct extension of the sample inlet line or lines (21) or, for zone electrophoresis, opposite the sample inlet on the other side of the longitudinal centre line of the flow bed (10).

11. An apparatus according to claim 9, wherein, for carrying out field jump electrophoresis, the sample inlet line (21) is arranged at the centre of the assembly of inlet channels (15) to the flow bed (10).

12. An apparatus according to claim 9, wherein, for isotachophoresis, an eccentric supply line (21) is provided for supplying the sample to the assembly of inlet channels 15 and two inlets (5) are provided for, different carrier liquids.

13. An apparatus according to claim 9, wherein for sample separation by means of electrophoresis with isoelectric focussing, in the region of the inlet channels (15), at both sides of the inlet of the supply line (21), that supply line is wound repeatedly about its path, and such windings (21a) are arranged at both sides of the inlet channels (15) in order to produce the focussing field.

14. An apparatus according to claim 9, wherein an outlet channel for uncharged or neutral compounds is arranged approximately in alignment with the inlet line (21) at the opposite end of the flow bed (10), and an outlet for charged compounds or ions is arranged laterally displaced with respect to the longitudinal centre line of the flow bed (10) and with respect to the inlet.

15. An apparatus according to claim 1, wherein the sample outlet (12) of a first flow bed (10) is connected to the sample inlet (6) of at least a second flow bed (10) for processing complex mixtures of different substances.

16. An apparatus according to claim 1, wherein the plate (8) comprising the flow bed (10), and/or the cover plate (9), consist of silicon and/or quartz and/or glass.

* * * * *